United States Patent [19]

Turner

[11] Patent Number: 4,627,726
[45] Date of Patent: Dec. 9, 1986

[54] METHOD AND APPARATUS USING LASER RADIATION FOR GENERATING AND MEASURING GAS BUBBLES

[75] Inventor: Robert Turner, Silver Springs, Md.

[73] Assignee: The Johns Hopkins University, Baltimore, Md.

[21] Appl. No.: 745,119

[22] Filed: Jun. 17, 1985

[51] Int. Cl.$^4$ ............................................. G01N 15/02
[52] U.S. Cl. ...................................... 356/336; 356/338
[58] Field of Search ..................... 356/336; 73/432 PS, 73/61, 19

[56] References Cited

U.S. PATENT DOCUMENTS

| | | | |
|---|---|---|---|
| 3,830,568 | 8/1974 | Allen | 356/336 |
| 4,211,487 | 7/1980 | Morrison et al. | 356/336 |
| 4,348,111 | 9/1982 | Goulas et al. | 356/338 |

OTHER PUBLICATIONS

"Measuring the Rate of Liquid Bubbling", Armitage, Jr., *IBM Technical Disclosure*, vol. 6, #4, 9/1963.

Primary Examiner—R. A. Rosenberger
Assistant Examiner—Crystal D. Cooper
Attorney, Agent, or Firm—Robert E. Archibald

[57] ABSTRACT

A non-intrusive method and apparatus for performing qualitative analysis of a liquid disposed within a container transparent to laser radiation comprises a first laser focused at a selected point within the liquid to produce or generate bubbles emanating from that location and a laser Doppler velocimeter which is intercepted by the rising bubbles to produce an output signal indicating both bubble size and velocity, as indication of liquid quality.

7 Claims, 2 Drawing Figures

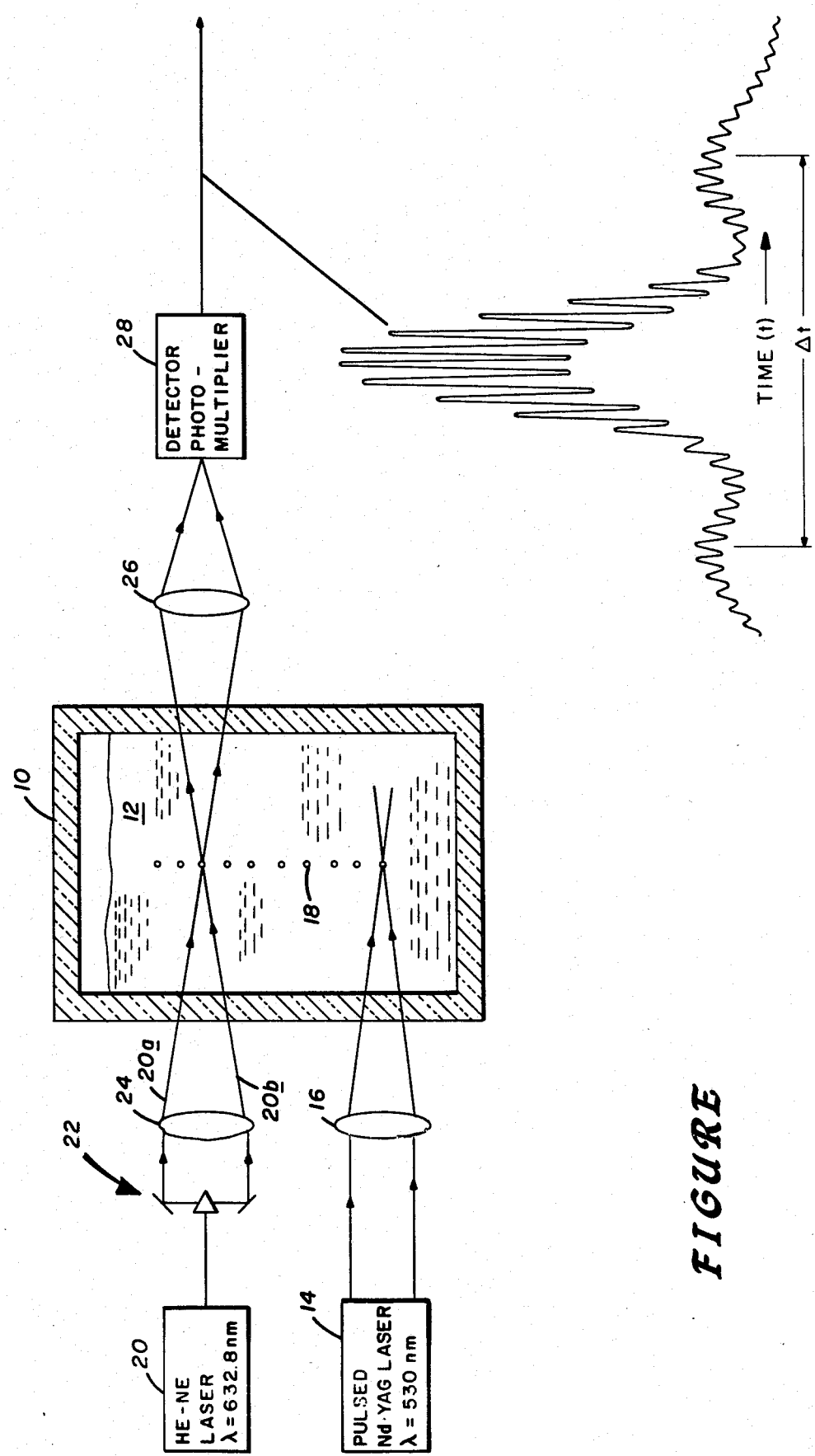
FIGURE

METHOD AND APPARATUS USING LASER RADIATION FOR GENERATING AND MEASURING GAS BUBBLES

STATEMENT OF GOVERNMENTAL INTEREST

The Government has rights in this invention pursuant to contract N00024-83-C-5301 awarded by the Department of the Navy.

BACKGROUND OF THE INVENTION

Within the past 15 years or so, modern optical techniques have been applied to the field of fluid mechanics, for example, for the purpose of analyzing the velocity of fluid flow and/or the distribution of particles or bubbles within the fluid.

The following three articles provide background of interest as regards the present invention. N. Ben-Yosef et al, in an article entitled Bubble size distribution measurement by Doppler velocimeter, Journal of Applied Physics, Vol. 46, No. 2, Feb. 1975, describe an experiment during which a laser Doppler velocimeter (LDV) was utilized to measure the velocity and size distribution of gas bubbles in water based upon the light scattering properties of the bubbles as they moved through the velocimeter laser beam from a bubble generator introduced into the bottom of a water column through appropriate mechanical fitting. Similarly, W. W. Martin et al, in their article Characteristics of Laser-Doppler Signals from Bubbles, appearing in the Int. J. Multiphase Flow, Vol. 7, pp. 439-460, (1981), also report on experiments aimed at measuring the signal characteristics of light scattered from single bubbles rising in quiescent water by means of laser-Doppler velocimetry. In this experiment, bubbles were investigated in the range of 200-1,000 micrometers and, as in the Ben-Yosef et al experiment, were generated by an air nozzle introduced at the bottom of the water column. This particular reference provides a detailed explanation of the triple-peaked laser-Doppler signal characteristic of the passage of a bubble through a dual-beam laser-Doppler velocimeter configuration. An article by W. Lauterborn et al entitled Modern Optical Techniques in Fluid Mechanics, Ann. Rev. Fluid Mech., pp. 223-244, published by Annual Reviews Inc. (1984) describes various optical techniques used in fluid mechanics to observe and measure properties of flow fields such as velocities and densities, and which describes briefly (at pp. 239 et seq.) the laser-induced formation of bubbles within a liquid.

Also of background interest is U.S. Pat. No. 4,348,111 to Goulas et al which discloses an optical particle analyzer that a generates a broad laser beam with a concentric narrow beam and a second, displaced narrow beam. The intensity and duration of the broad light beam reflected by individual particles within a particle stream indicates particle size. The concentric narrow beam is used to validate the passing of a particle through the broad beam's center. Time delay between interception of the concentric and displaced narrow beams is used to determine particle velocity. U.S. Pat. No., 4,211,487 to Morrison et al discloses an apparatus for determining aerosol size distribution, utilizing laser technology. A first laser directs an amplitude modulated beam through the aerosol distribution in question, such that droplets of a particular size are sequentially resonated. A second laser beam is directed against the oscillating droplets, is scattered thereby and then monitored in order to analyze droplet size distributions within the aerosol.

SUMMARY OF THE INVENTION

It is proposed in accordance with the present invention to apply laser technology for the purpose of achieving a non-intrusive method and apparatus for performing qualitative analysis of a liquid disposed within a container transparent to the laser radiation used. More specifically, in the illustrated embodiment to be described hereinafter, laser technology is utilized both for generating gas bubbles from gas dissolved within a contained liquid and subsequently measuring their size(s) with a laser Doppler velocimeter. Applications for the present invention include in general the measurement of the properties of liquids containing dissolved gases, as well as the specific use for accomplishing non-intrusive testing of bottled carbonated beverages, for example, to evaluate different methods or amounts of carbonation.

Although the aforementioned prior art indicates the separate use of laser technology to generate bubbles and to measure their velocity and size distribution, based upon the light scattering properties of the bubbles as they pass through the detection volume of a laser Doppler velocimeter, the present inventor has proposed a novel combination of these technologies for the novel application to the particular problem of non-intrusively analyzing the quality of liquids in an optically transparent container, e.g. for the purpose of sensing whether an appropriate or desired level of carbonation is present.

Accordingly, an object of the present invention is to provide a method and apparatus utilizing laser technology to generate gas bubbles and to measure their size(s) in liquids disposed within containers that are transparent to the laser radiation.

Another objective of the present invention is to provide a non-intrusive system for measuring the quality of a liquid disposed within a container transparent to laser radiation.

A further object of the present invention is to provide a non-intrusive method and apparatus, utilizing a laser source to generate bubbles within a liquid containing dissolved gas and a laser Doppler velocimeter to measure the rising velocity of the bubbles and their corresponding size as a measure of the properties of the liquid in which the bubbles are generated.

A still further object of the invention is to provide an optical system for measuring non-intrusively the quality of a liquid containing dissolved gas therein and disposed within an optically transparent container.

Further objects, purposes and characteristic features of the present invention will, in part, be pointed out as the description of the invention progresses and, in part, be obvious from the accompanying drawings wherein the illustrated figure shows the currently preferred embodiment of the present invention, utilizing laser technology to non-intrusively generate bubbles within a contained body of liquid having gas dissolved therein and subsequently to measure the velocity and size of those bubbles as a measure of the overall quality or of certain selected properties of the liquid.

Referring now to the accompanying drawing, container 10 includes a liquid 12 having dissolved gasses therein. For example, in one practical application of the present invention, the container 10 might be a bottle containing a carbonated beverage whose quality is to be tested.

In accordance with the present invention, a pulsed Nd.YAG laser 14, at a wavelength (λ) of 530 nanometers, is positioned adjacent to the container 10 (which is transparent to the laser radiation) and its output laser beam is focused by means of lens 16 at a preselected, localized point within the liquid 12. As a result, the focused laser radiation heats the liquid 12 locally to release the entrapped gas and thus generate bubbles 18 emanating from the local point within the liquid 12. These bubbles migrate upward within the liquid 12 at a velocity that is proportional to their diameter; i.e. larger bubbles rise more rapidly than smaller bubbles.

In order to non-intrusively measure the rising velocity of the bubbles 18, a dual-beam laser Doppler velocimeter is utilized, comprising an HE-NE laser 20, at wavelength (λ) of 632.8 nanometers, beam splitter 22, lenses 24 and 26 and detector/photomultiplier unit 28.

More particularly, the illustrated laser Doppler velocimeter (LDV) is a conventional measuring instrument which utilizes the scattered light pattern produced by a bubble, as it passes through the intersection of the two laser beams, to produce an output signal indicative of bubble velocity and size. A typical triple-peaked laser-Doppler signal output from the detector photomultiplier unit 28 is shown in the accompanying figure. The spacing ($\Delta t$) between the outer peaks of the output signal is related to the diameter (d) of the passing bubble by the expression $d = V \cdot \Delta t$, where V is the bubble velocity; whereas, the frequency of the center peak in the output signal is proportional to the bubble velocity as it passes through the detection volume of the LDV. In one practical application of the present invention, an LDV comprised of a TSI Inc. model no. 9100-1 was utilized following modification to lower the frequency response from a nominal 2 kilohertz to approximately DC level.

The size of the bubbles in a carbonated beverage and the rate at which the bubbles are released when the beverage is drunk is a matter of concern to beverage makers. There is a wide range of claims or statements about the advantages of a particular method of carbonation, and the relationship between bubble size and the quality of the product. In particular, companies refer to pinpoint carbonation, or natural carbonation as producing better beverages, or that better beers especially have smaller bubbles. As far as is known, all such statements are subjective, and a need exists for a more objective method to detect bubble size. One previously suggested method of rating the quality of carbonations, for example, is to rate the so-called "mouthfeel" (harsh, explosive, etc.) of the beverage when it is drunk. The methods that are used to carbonate a beverage are also of commercial concern and there is a need for a more objective technique to determine the differences between them.

In light of the foregoing disclosure, it should be obvious that the present invention may be practiced otherwise than as specifically described. Other modifications, adaptations and alterations are thus possible within the scope of the appended claims.

What is claimed is:

1. A non-intrusive system for measuring the quality of a liquid disposed within a container transparent to laser radiation comprising, in combination, a first laser means external to said container producing a laser beam focused at a predetermined location within said liquid, said focused laser beam heating said liquid locally to generate bubbles from gas dissolved within said liquid, said bubbles migrating upwardly from said predetermined location at a velocity which varies in proportion to bubble size, and a laser Doppler velocimeter including second laser means external to said container producing a pair of intersecting laser beams traversed by said migrating bubbles and a detector photomultiplier means generating an output electrical signal indicative of the velocity and the diameter of said bubbles as a measure of liquid quality.

2. The system specified in claim 1 wherein said first laser means includes a pulsed Nd.YAG laser at a wavelength of 530 nanometers, and said second laser means includes a continuous HE-NE laser at a wavelength of 632.8 nanometers and a beam-splitter and lens combination for converting the output beam of said HE-NE laser into a pair of intersecting laser beams.

3. The system specified in claim 1 wherein said first laser means includes a laser generating an output beam and a lens aligned optically with the output of said laser for focusing said output beam at said predetermined location within said liquid.

4. The system specified in claim 1 wherein said output electrical signal associated with each bubble traversing said intersecting laser beams of said laser-Doppler velocimeter is a triple-peaked laser Doppler signal having outer peaks whose spacing varies in proportion to bubble diameter divided by the bubble velocity and a frequency component which varies in proportion to bubble velocity.

5. An optical system for measuring non-intrusively the quality of a liquid containing dissolved gas therein and disposed within an optically transparent container comprising, in combination, a first energy source at optical frequency located external to said container for transmitting a focused optical beam through said container towards a preselected location within said liquid, said focused optical beam producing localized heating at said preselected location to generate bubbles which rise within said liquid from said preselected location, a second energy source at optical frequency located external to said container for transmitting an optical beam through said container and said liquid, said rising bubbles each intersecting said optical beam from said second source and producing light scattering dependent upon the size and velocity thereof, and detector means positioned external to said container to receive the optical beam from said second source after transmission through said liquid and container for producing an output electrical signal for each bubble indicative of said light scattering produced thereby.

6. The system specified in claim 5 wherein said first energy source is a pulsed Nd.YAG laser operated at a wavelength of 530 nanometers.

7. The system specified in claim 5 wherein said second energy source is a continuous HE-NE laser operated at a wavelength of 632.8 nanometers and forming part of a laser-Doppler anemometer for detecting the size and velocity of said rising bubbles.

* * * * *